United States Patent
Berlat

(10) Patent No.: US 8,263,114 B2
(45) Date of Patent: Sep. 11, 2012

(54) TOPICAL PHARMACEUTICAL FORMULATION

(75) Inventor: Alvin Berlat, Silverdale, WA (US)

(73) Assignee: Advanced Bio-Technologies, Inc., Suwanee, GA (US)

( * ) Notice: Subject to any disclaimer, the term of this patent is extended or adjusted under 35 U.S.C. 154(b) by 1875 days.

(21) Appl. No.: 10/480,719

(22) PCT Filed: Jul. 23, 2002

(86) PCT No.: PCT/GB02/03387
§ 371 (c)(1), (2), (4) Date: Jul. 8, 2004

(87) PCT Pub. No.: WO03/009877
PCT Pub. Date: Feb. 6, 2003

(65) Prior Publication Data
US 2004/0234474 A1    Nov. 25, 2004

(51) Int. Cl.
*A61F 13/00* (2006.01)
*A61K 9/70* (2006.01)
*A61L 15/00* (2006.01)
*A61L 15/16* (2006.01)

(52) U.S. Cl. .......... 424/443; 424/445; 424/446

(58) Field of Classification Search ........ 424/443, 424/448, 449, 445, 323, 446–447; 514/944, 514/969; 428/323; 128/898, 893
See application file for complete search history.

(56) References Cited

U.S. PATENT DOCUMENTS

| | | | |
|---|---|---|---|
| 5,292,530 A * | 3/1994 | McCrea et al. | 424/66 |
| 5,389,092 A | 2/1995 | Guillemet et al. | |
| 5,556,699 A * | 9/1996 | Niira et al. | 428/323 |
| 5,741,509 A * | 4/1998 | Kushner | 424/443 |
| 5,833,998 A | 11/1998 | Biedermann et al. | |
| 5,972,320 A | 10/1999 | Moloney | |
| 6,155,265 A * | 12/2000 | Hammerslag | 128/898 |
| 6,183,766 B1 | 2/2001 | Sine et al. | |
| 6,827,929 B1 | 12/2004 | Lord et al. | |
| 2006/0110415 A1 | 5/2006 | Gupta | |
| 2008/0292560 A1 | 11/2008 | Tamarkin et al. | |
| 2008/0299220 A1 | 12/2008 | Tamarkin et al. | |
| 2009/0143333 A1 | 6/2009 | Palefsky et al. | |

FOREIGN PATENT DOCUMENTS

| | | |
|---|---|---|
| JP | 04-009327 | 1/1992 |
| JP | 09-194350 | 7/1997 |
| WO | WO 97/03710 | 2/1997 |
| WO | WO-00/47183 | 8/2000 |
| WO | WO 00/47183 | 8/2000 |
| WO | WO-01/89464 | 11/2001 |

OTHER PUBLICATIONS

U.S. Appl. No. 10/479,877, filed May 2004, Berlat, A.*
Thixin R/ Thixcin R—properties bulletin; Elementis Specialities, Inc.
Merck Index (9th Ed.) Entry No. 9812: Zinc Oxide.
Dow Corning MSDS for silicone blend 225 (i.e. DC-225).

* cited by examiner

Primary Examiner — Johann Richter
Assistant Examiner — Mei-Ping Chui
(74) Attorney, Agent, or Firm — Shumaker, Loop & Kendrick, LLP

(57) ABSTRACT

A composition comprising a non-volatile silicone fluid in admixture with fumed silica and a pharmaceutical active agent.

37 Claims, No Drawings

TOPICAL PHARMACEUTICAL FORMULATION

The present invention relates to silicone based compositions, a method of manufacturing such compositions and the use of such compositions in medicine. In particular, although not exclusively, the present invention provides a silicone based wound dressing comprising a pharmaceutical active agent for the curative and/or prophylactic treatment of a medical condition.

Damage to the skin, for example produced by injury or surgery, may produce wounds which are susceptible to infection by pathogens, such as viruses and bacteria. Suitably, it may be necessary to treat such wounds with one or more pharmaceutical active agents, such as an antibiotic, anti-viral and/or antifungal compound in the hope of alleviating or preventing infection of the wound. Although such pharmaceutical active agents may be administered by various routes, such as oral or topical administration, topical administration of the active agent represents a convenient and effective mode of administration for the patient.

Although, pharmaceutical gel and cream formulations for delivering a therapeutic effective amount of a drug to a target tissue by topical administration are known, the universal applicability of these formulations to treat a particular target tissue site, in particular a wound, may be restricted for a number of reasons. In particular, topical pharmaceutical preparations may require complex formulations so that a therapeutic effective amount of the pharmaceutical active agent is delivered to the target tissue (for example wounds, cuts or skin lesions) whilst minimising undesirable side effects, such as irritation of the skin and mucosa. Complex formulations may also be required to prevent degradation of the active agent in the formulation and/or minimise physical instability of the formulation itself (e.g. separation of the component parts, thickening precipitation/agglomerization of the active agent). Such problems may be further enhanced when the pharmaceutical active agent is a solid that is substantially in soluble in common pharmaceutical diluents/carriers etc. Suitably, such solid pharmaceutical active agents may necessitate particularly complex formulations. A still further potential problem with known topical pharmaceutical formulations which may render them unsuitable for application to a wound, such as skin lesion or cut, is that such formulations may prevent normal skin function, they may suppress the normal immune response and they may allow pathogens, such as bacteria, to evolve around the barriers which they provide.

In addition to the likelihood of infection, damage to the skin produced by injury or surgery may produce scars instead of regenerating the original tissue. Such scars are typically undesirable as they may create embarrassing cosmetic problems and the scar tissue typically lacks the functionality of normal skin. For example, the sense of touch may be diminished or completely lost and weak spots may form where the scar tissue joins uninjured tissue. Suitably, a wound dressing adapted to reduce, prevent and/or ameliorate scar formation may be applied to the target tissue or scar, respectively.

Typically, treatment regimes for reducing or preventing infection of a wound include the application of an antibiotic formulation, for example an antibiotic ointment, to the wound followed by the application of a covering, such as a bandage, to enhance contact of the ointment around the wound. Suitably, these coverings may include an adhesive for retaining the covering in position. Unfortunately, the presence of an adhesive may cause an allergic reaction which may negatively effect the healing process.

In order to prevent or reduce infection and/or scar formation of a wound it is usually necessary to apply a separate pharmaceutical active agent, such as an antibiotic ointment, and thereafter a wound dressing or covering designed to reduce or prevent scar formation. A problem associated with such treatment methods is that the regime involves two steps; the application of the antibiotic followed by the separate application of the wound dressing or covering. Suitably, if it is necessary to apply a further amount of the pharmaceutical active agent to the wounded tissue, then the wound dressing will have to be removed and the above two steps repeated. Inconveniently, this may not only reduce patient compliance but may inflict further damage to the injured tissue and further pain to the patient.

The present invention therefore seeks to provide improved compositions suitable for application to a target tissue site, in particular a target tissue site that it is susceptible to pathogenic infection and/or scarring, especially to a skin lesion or wound.

According to a first aspect, the present invention provides a composition comprising a non-volatile silicone fluid in admixture with fumed silica, and a pharmaceutical active agent. Such a composition is referred to hereinafter as the composition of the present invention.

Suitably, the composition of the present invention seeks to solve the aforementioned technical problems associated with treating a wound. In particular, the mixture of the non-volatile silicone fluid and fumed silica in the composition of the present invention may act as a suitable vehicle to permit a therapeutic effective amount of the pharmaceutical active agent to be delivered to and retained by a target tissue site (i.e. skin lesion or cut). Suitably, the pharmaceutical active agent does not degrade and typically exhibits physical stability in the composition of the present invention. For example, the components of the composition may not separate and the pharmaceutical active agent may not precipitate/agglomerize. Suitably, the composition of the present invention does not require an additional adhesive to retain it in position on the target tissue site, thereby minimising allergic reactions which may negatively effect the healing process.

Suitably, the composition of the present invention is dual purpose as it may be used as a wound dressing to reduce, prevent or ameliorate scarring of damaged tissue and/or it also may be used for the topical delivery of a pharmaceutical active agent to the tissue. Consequently, the composition of the present invention enables a pharmaceutical active agent and a wound dressing/covering to be applied to a target tissue in a single step thereby increasing patient compliance compared with a two step regime which involves the separate application of a pharmaceutical active agent followed by application of a separate wound dressing. It will be appreciated that the composition of the present invention may be applied by medical and non-medical professional staff, as it is straightforward to apply. Such methods of application by non-medical professional staff are embraced by the methods of the present invention as described hereinafter.

Suitably, the composition of the present invention may negate the need for a complex formulation of the pharmaceutical active agent to ensure that a therapeutic effective amount of the active agent is delivered to the target tissue when the patient moves, as the blend of the non-volatile silicone fluid and the fumed silica typically acts as a carrier for the pharmaceutical active agent and typically has a suitable viscosity to adhere to the target tissue.

Suitably, the activity of the pharmaceutical active agent in the composition of the present invention may be enhanced compared to employing the unmodified pharmaceutical active agent alone. Moreover, pharmaceutical active agents in the form of powders and liquids, may be used in the composition of the present invention without the need for further processing. Consequently, the composition of the present invention may overcome problems associated with delivering a therapeutic effective amount of a liquid or solid pharmaceutical active agent to a target tissue (i.e. delivering and retaining the active agent at the target site for sufficient time to enable the active agent to have the desired effect) whilst increasing the efficacy of the active agent.

Suitably, the composition of the present invention may exhibit increased reduction and/or prevention of scars when applied to a target tissue (i.e. wound) compared to a substantially identical composition not including the pharmaceutical active agent.

As mentioned previously, pharmaceutical active agents in the form of a powder or liquid themselves, particularly a powder, typically require complex formulations so that they may be applied topically to a target tissue site. Moreover, a separate cover, such as a wound dressing, is typically required to retain the pharmaceutical active agent at the target tissue site. For example, as a powder is very fragile and easily removed from the skin an adhesive plaster is usually used to retain the powder, or a formulation thereof, at the target site. However, the adhesive may irritate the target site and the process of normal skin activity may also be impaired i.e. it may prevent the skin from allowing the passage of water vapour, gases and toxins therefrom. Although only theory, it is believed that any increased efficacy of a pharmaceutical active agent, such as an antibacterial agent, when incorporated in a mixture of non-volatile silicone fluid and fumed silica may not only be due to the mixture of non-volatile silicone fluid and fumed silica retaining and delivering the active agent to the target tissue site but also may be due to the mixture of non-volatile silicone fluid and fumed silica allowing the target site (i.e. skin) to function normally. In particular, although the mixture of non-volatile silicone fluid and fumed silica in itself does not appear to possess antibacterial activity, it is believed that when it is applied to the skin it provides a barrier to potential pathogens and because it is hydrophobic it allows the skin to function normally i.e. it permits the passage of water vapour, gases and toxins therefrom, thereby enhancing the effect of the pharmaceutical active agent. Suitably, the composition of the present invention may possess antibacterial, antiviral and/or antifungal activity. Suitably, the composition of the present invention may promote normal skin function without suppressing the normal immune response. Suitably, the composition of the present invention may not irritate the target tissue. Still further, the composition of the present invention typically does not require professional attention for proper maintenance, particularly for a minor wound.

By the term "non-volatile silicone fluid" we include a silicone fluid that does not substantially evaporate from the composition of the present invention at normal body temperature (i.e. up to and including 38° C.) and atmospheric pressure. Preferably, the non-volatile silicone fluid does not substantially evaporate from the composition at room temperature (i.e. up to and including 25° C.) and at atmospheric pressure.

Suitably, the non-volatile silicone fluid per se does not exhibit an appreciable vapour pressure at ambient temperature. Preferably, the volatile content of the non-volatile silicone fluid per se at 150° C. is less than or equal to 0.8% by weight, more preferably less than or equal to 0.6% by weight, even more preferably less than or equal to 0.4% by weight, most preferably less than or equal to 0.3% by weight based on the total weight of the non-volatile silicone fluid per se.

Suitably, the non-volatile silicone fluid component forms the base for the composition of the present invention and provides the chemical properties of the barrier between the injured target tissue and the environment. Suitably, the non-volatile silicone fluid is a silicone polymer.

Preferably, the non-volatile silicone fluid is a non-volatile silicone oil. Preferably, the non-volatile silicone fluid has a viscosity at 25° C. of greater than or equal to 500 centistokes, more preferably greater than or equal to 5,000 centistokes, most preferably greater than or equal to 10,000 centistokes when measured by ASTM D-445, IP71 using a glass capillary viscometer such as an Ubbelohde available from Fisher Scientific Co., Pittsburgh, Pa., USA. Preferably, the silicone fluid has a viscosity at 25° C. of less than or equal to 200,000 centistokes, more preferably less than or equal to 100,000 centistokes, most preferably less than or equal to 50,000 centistokes. Suitably, viscosities up to 100,000 centistokes may be measured by ASTM D-45, IP71 using a glass capillary viscometer. Viscosities above 100,000 centistokes may be measured using rotational viscometers such as a Brookfield Synchro-lectric viscometer or a Wells-Brookfield Core/Plate viscometer available from Brookfield Engineering Laboratories, Stoughton, Mass., USA employing test methods ASTM D-1084 (for a cup/spindle viscometer) and ASTM D-4287 (for a cone/plate viscometer). Suitably, when measuring viscosities above 100,000 centistokes, viscometers designed for the high viscosity region (HA and HB models) are employed. Highly preferred non-volatile silicone fluids have a viscosity at 25° C. of about 30,000 centistokes when measured by ASTM D-445, IP71 using a glass capillary viscometer.

Preferably, the non-volatile silicone fluid comprises a silicone polymer, particularly a linear silicone polymer, especially a linear dimethicone polymer. Highly preferred non-volatile silicone fluids comprise a polydimethyl-siloxane polymer, especially a linear polydimethylsiloxane polymer.

It will be appreciated that by increasing the viscosity of the non-volatile silicone fluid in the composition of the invention may produce a composition having increased durability and resistance to removal from the target tissue site, particularly following evaporation of the volatile diluent as described hereinafter from the composition if one is used. Similarly, by lowering the viscosity of the non-volatile silicone fluid component produces a composition which may be more easily applied to and removed from the target tissue. By using the full range of silicone oil viscosities, the composition of the present invention may be tailored to the unique needs of each case. Silicone fluids having viscosities at 25° C. of about 30,000 centistokes are especially preferred as they provide a balance of residual durability and ease of applicability. A particularly preferred non-volatile silicone fluid is Dow Corning 200 having a viscosity at 25° C. of about 30,000 centistokes produced by Dow Corning Inc. (Midland, Mich.).

Preferably, the non-volatile silicone fluid is present in an amount of greater than or equal to 20% by weight, more preferably greater than or equal to 30% by weight, even more preferably greater than or equal to 40% by weight, even more preferably greater than or equal to 50% by weight, even more preferably greater than or equal to 60% by weight, even more preferably greater than or equal to 70% by weight, even more preferably greater than or equal to 80% by weight, even more preferably greater than or equal to 85% by weight, most preferably greater than or equal to 90% by weight based on the total weight of the composition of the present invention. Preferably, the non-volatile silicone fluid is present in an amount of less than or equal to 99% by weight, more preferably less than or equal to 97% by weight, even more preferably less than or equal to 95% by weight based on the total weight of the composition of the present invention.

Suitably, the fumed silica provides a micro-skeletal structure when dispersed in the non-volatile silicone fluid to provide a gel. Preferably, the fumed silica is amorphous. The viscosity of the original non-volatile silicone fluid may be dramatically increased when mixed (e.g. blended) with suitable quantities of fumed silica to form, for example a non-fluid grease-like gel. Any amorphous fumed silica that suitably thickens the non-volatile silicone fluid component may be used. Such fumed silicas include both untreated types and types that have been chemically treated to alter the fumed silica surface. Examples of suitable fumed silicas include but are not limited to Aerosil™ 90, 130, 200, 300, 380, R202, R805, R812, R972, R974 (Degussa Corporation, Ridgefield Park, N.J.) and CAB-O-SIL™ TS-720 and M-5 (Cabot Corporation, Tuscola, Ill.). Generally, Aerosil™ 200, Aerosil™ R974, CAB-O-SIL™ TS-720 and any other generally equivalent products from other manufacturers of fumed silicas are preferred as they suitably thicken non-volatile silicone fluids. Typically, the larger the quantity of fumed silica in the blend, the more viscous is the resultant gel.

Preferably, the fumed silica is present in an amount of greater than or equal to 0.25% by weight, more preferably greater than or equal to 0.5% by weight, even more preferably greater than or equal to 1% by weight, most preferably greater than or equal to 2% by weight based on the total weight of the composition of the present invention. Preferably, the fumed silica is present in an amount of less than or equal to 10% by weight, more preferably less than or equal to 8% by weight, even more preferably less than or equal to 6% by weight, most preferably less than or equal to 5% by weight based on the total weight of the composition of the present invention. A particularly preferred composition of the present invention comprises approximately 3% by weight fumed silica based on the total weight of the composition of the present invention.

Preferably, in the composition of the present invention the blend of non-volatile silicone fluid and fumed silica comprises from greater than or equal to 0.25%, more preferably greater than or equal to 0.5%, most preferably greater than or equal to 1% by weight fumed silica. Preferably, in the composition of the present invention the blend of non-volatile silicone fluid and fumed silica comprises less than or equal to 12%, more preferably less than or equal to 9%, most preferably less than or equal to 5% by weight fumed silica. Such compositions typically provide a balance of thickness and workability.

Preferably, in the composition of the present invention the blend of non-volatile silicone fluid and fumed silica comprises from less than or equal to 99.75%, more preferably less than or equal to 99.5%, most preferably less than or equal to 99% by weight non-volatile silicone fluid. Preferably, in the composition of the present invention the blend of non-volatile silicone fluid and fumed silica comprises greater than or equal to 88%, more preferably greater than or equal to 91%, most preferably greater than or equal to 95% by weight non-volatile silicone fluid.

Preferably, in the composition of the present invention the blend of the non-volatile silicone fluid and fumed silica is present in an amount of greater than or equal to 1%, preferably greater than or equal to 22%, preferably greater than or equal to 24.9%, preferably greater than or equal to 47%, preferably greater than or equal to 49.9%, preferably greater than or equal to 57%, preferably greater than or equal to 59.9%, preferably greater than or equal to 62%, preferably greater than or equal to 64.9% by weight of the composition of the present invention. Preferably, in the composition of the present invention the blend of the non-volatile silicone fluid and fumed silica is present in an amount of less than or equal to 98.9%, preferably less than or equal to 96%, preferably less than or equal to 94.9%, preferably less than or equal to 92%, preferably less than or equal to 89.9%, preferably less than or equal to 87%, preferably less than or equal to 84.9%, preferably less than or equal to 82%, preferably less than or equal to 79.9%, preferably less than or equal to 77%, preferably less than or equal to 74.9%, preferably less than or equal to 72% by weight of the composition of the present invention.

The composition of the present invention may also include pharmaceutically acceptable adjuvants for the treatment of skin lesions, such as coal tar and salicylic acid.

By the term "pharmaceutical active agent" we include any compound, including pharmaceutical acceptable derivatives such as a salt, solvate and pro-drug and any composition which may be used for the curative and/or prophylactic treatment of a medical condition of a human or animal. Preferably, the pharmaceutical active agent possesses antibacterial, antiviral and/or antifungal activity. More preferably, the pharmaceutical active agent comprises an antibacterial agent.

Suitably, the pharmaceutical active agent may be in the form of a liquid, gel or powder. Preferably, the pharmaceutical active agent is in the form of a solid, particularly a powder, especially a powder that is insoluble in typical pharmaceutical acceptable diluents, such as water or alcohols.

Preferred antibacterial agents include antibiotic zeolites, chlorohexidine, polymyxin B sulphate, benzachromium chloride, benzamycin, clindamycin, erythromycin, tetracycline, mupirocin, bacitracin zinc and neomycin sulphate. Especially preferred antibacterial agents include antibiotic zeolites.

Preferred antibiotic zeolites include those in which the ion-exchangeable ions of the zeolite such as sodium ions, potassium ions, calcium ions, magnesium ions and iron ions have been partially or completely ion-exchanged with antibiotic ions. Examples of suitable antibiotic ions include silver, copper, zinc, mercury, tin, lead, bismuth, cadmium, chromium and thallium ions. Preferred antibiotic metal ions are silver, copper and zinc ions. These ions may be used alone or in combination. A particularly preferred antibiotic ion is silver.

Either natural or synthetic zeolites may be used as the "zeolite component". Examples of such zeolites are disclosed in U.S. Pat. No. 5,556,699 which is incorporated herein by reference. Methods for preparing the antibiotic zeolites for use in the composition of the present invention may be prepared by techniques well known to those skilled in the art, for example, as disclosed in U.S. Pat. No. 5,556,699.

Preferably, the antibiotic metal ions are present in the zeolite in an amount of greater than or equal to 0.1%, preferably greater than or equal to 0.25%, more preferably greater than or equal to 0.75%, most preferably greater than or equal to 1% by weight of the zeolite. Preferably, the antibiotic metal ions in the zeolite is present in an amount of less than or equal to 15%, more preferably less than or equal to 10%, most preferably less than or equal to 5% by weight of the zeolite. By the term % by weight of the zeolite we mean expressed in terms of the weight of the zeolite weighed after drying at a temperature 110° C.

Preferably, the pharmaceutical active agent is present in an amount of less than or equal to 50%, more preferably less than or equal to 30%, more preferably less than or equal to 10%, most preferably less than or equal to 3% by weight of the composition. Preferably, the pharmaceutical active agent is present in an amount of greater than or equal to 0.1%, more preferably greater than or equal to 0.5%, especially greater than or equal to 1.0% by weight of the composition.

It will be appreciated by those skilled in the art that although antibiotic zeolites possess suitable antibiotic activity they typically require complex formulations in order to make them suitable for application, particularly topical application, to a target tissue. Surprisingly, it has been found that an antibiotic zeolite may be incorporated into the blend of the non-volatile silicone fluid and fumed silica blend, with or without a diluent as described hereinafter, without the need for further complicated processing techniques. Moreover, the resultant composition of the present invention comprising the antibiotic zeolite may exhibit enhanced antibacterial activity compared with the antibiotic zeolite alone.

Conveniently, the composition of the present invention may be regarded as a dual-purpose composition, as it may be employed for the prophylactic and/or reduction in scar tissue as well as the prophylactic and/or reduction of infection.

Preferably, the composition of the present invention further includes a diluent.

By the term "diluent" we include a vehicle that dissolves or disperses the non-volatile silicone fluid and fumed silica blend and thus reduces the viscosity of the blend. Preferably the diluent is a volatile diluent. The volatile diluent preferably evaporates at normal body temperature (i.e. up to and including 38° C.) and atmospheric pressure. More preferably, the volatile diluent evaporates at room temperature (i.e. up to and including 25° C.) and atmospheric pressure.

Suitably, the volatile diluent exhibits appreciable vapour pressure at ambient temperature. Preferably, the volatile diluent exhibits a heat of vaporization at 25° C. of greater than or equal to 50 kJkg$^{-1}$, more preferably greater than or equal to 75 kJkg$^{-1}$, even more preferably greater than or equal to 100 kJkg$^{-1}$, most preferably greater than or equal to 125 kJkg$^{-1}$. Preferably, the volatile diluent exhibits a heat of vaporization at 25° C. of less than or equal to 275 kJkg$^{-1}$, more preferably less than or equal to 250 kJkg$^{-1}$, even more preferably less than or equal to 225 kJkg$^{-1}$, most preferably less than or equal to 200 kJkg$^{-1}$.

Suitably, the volatile diluent exhibits a low viscosity when measured at 25° C. The viscosity of the volatile diluent may be measured using a glass capillary viscometer such as a Ubbelohde available from Fisher Scientific Co., Pittsburgh, Pa., USA, employing test method ASTM D-445, IP71.

Preferably, the volatile diluent has a kinematic viscosity of greater than or equal to 0.5 mm$^2$s$^{-1}$, more preferably greater than or equal to 2 mm$^2$s$^{-1}$, particularly greater than or equal to 3 mm$^2$s$^{-1}$ when measured in accordance with the above method. Preferably, the volatile diluent has a viscosity of less than or equal to 10 mm$^2$s$^{-1}$, more preferably less than or equal to 9 mm$^2$s$^{-1}$, particularly less than or equal to 8 mm$^2$s$^{-1}$ at 25° C. when measured in accordance with the above method.

Preferably, the diluent is a silicone fluid (such as a liquid) as these are typically compatible with the non-volatile silicone fluid. Preferably, the volatile diluent is a volatile silicone fluid. Suitably, the volatile silicone fluid comprises a silicone polymer, particularly a cyclomethicone silicone polymer. Preferred silicone polymers are selected from polydimethylcyclosiloxane, polymethyldisiloxane, octamethylcyclo-tetrasiloxane, hexamethyldisiloxane, dimethylcyclo-siloxane, dodecamethylcyclohexasiloxane, decamethylcyclo-tetrasiloxane or octamethyltrisiloxane or a mixture thereof.

Examples of suitable volatile silicone fluids are Dow-Corning 244 which comprises a cyclomethicone octamethylcyclotetrasiloxane, Dow-Corning 245 which comprises a cyclomethicone decamethylcyclopentasiloxane Dow Corning 246 which comprises a cyclomethicone dodecamethyl cyclohexasiloxane and Dow Corning 345 which comprises a cyclomethicone decamethylcyclopentasiloxane.

Mixtures of volatile silicone fluids may also be used to alter the rate of volatilization if desired. The volatile component may be added to the mixture of non-volatile silicone fluid and fumed silica in any proportion required to reduce the viscosity to an easy to apply oil or light grease. At very high dilution, for example if 1 part by weight of a blend of non-volatile silicone fluid and fumed silica is added to 1000 parts by weight of the volatile diluent, then the product can be applied as a mobile fluid with a suitable applicator, such as a roll-on applicator, or even as a spray from a spray bottle. At the other extreme, as little as 1 part by weight of the volatile diluent may be added to 99 parts by weight of the non-volatile silicone and fumed silica blends to produce a more viscous composition to assist in its application.

Suitably, when present, the diluent is present at greater than or equal to 1%, preferably greater than or equal to 5%, preferably greater than or equal to 10%, even more preferably greater than or equal to 15%, even more preferably greater than or equal to 20%, most preferably greater than or equal to 25% by weight, even more preferably greater than or equal to 30% by weight, most preferably greater than or equal to 35% by weight based on the total weight of the composition of the present invention. Suitably, when present, the diluent is present at less than or equal to 99.9%, preferably less than or equal to 75%, even more preferably less than or equal to 50% by weight based on the total weight of the composition of the present invention.

Suitably, when a diluent is included in the composition of the present invention, then the diluent may form substantially the balance of the composition of the present invention.

Suitably, when a diluent is included in the composition of the present invention, the non-volatile silicone fluid as described herein is present in an amount of greater than or equal to 20% by weight, more preferably greater than or equal to 25% by weight, even more preferably greater than or equal to 30% by weight, most preferably greater than or equal to 35% by weight based on the total weight of the composition of the present invention. Suitably, when a diluent is included in the composition of the present invention, the non-volatile silicone fluid as described herein is present in an amount of less than or equal to 65% by weight, more preferably less than or equal to 60% by weight, even more preferably less than or equal to 55% by weight based on the total weight of the composition of the present invention.

For the avoidance of doubt, when a diluent is included in the composition of the present invention, the amount of pharmaceutical active agent and fumed silica present in the composition is preferably within the preferred ranges as defined hereinbefore.

It will be appreciated that a volatile diluent may be employed instead of or in conjunction with a non-volatile diluent so that the total amount of diluent in the composition of the present invention is within the aforementioned stated ranges.

Suitably, the blend of the non-volatile silicone fluid and fumed silica has a higher viscosity than the composition of the present invention and the diluent i.e. a composition comprising the blend of the non-volatile silicone fluid and fumed silica, the diluent and the pharmaceutical active agent. Consequently, a composition of the present invention including the diluent may be prepared in the form of a spreadable cream, gel, oil or light grease which can be applied to a wound without producing further injury of discomfort. Suitably, if a volatile diluent is employed in the composition of the present invention, after the blend is in place on the wound, evaporation of the volatile diluent therefrom, produces a resultant composition typically having an increased viscosity that is substantially equivalent to that of the blend of the non-volatile silicone fluid and fumed silica alone. In other words, a coating having a viscosity of a stiff cream or grease may be formed from a spreadable cream, thereby providing increased wound adhesion and smear proofing, without producing further damage to the wound or undue pain and discomfort during application. Furthermore, upon evaporation of the volatile diluent the pharmaceutical active agent typically becomes sequestered within the composition of the present invention i.e. the active agent is retained by the composition and delivered topically therefrom to the target tissue.

It will be appreciated by those skilled in the art that the consistency of the blend of the non-volatile silicone fluid and fumed silica may be adjusted by varying the quantity of the diluent present therein. Consequently the composition of the present invention including the diluent may be in the form of films and sheets, as well as a spreadable cream, gel, oil or light grease. Typically, the physical and chemical properties of the residual non-volatile silicone fluid and fumed silica blend and pharmaceutical active agent are unaltered after evaporation of the volatile diluent. However, it will be appreciated, particularly for highly viscous silicone fluid and fumed silica blends, that traces of the volatile diluent may remain in the composition after application which may eventually be driven off by body heat.

Preferably, the composition of the present invention is in the form of a gel or cream. Typically, when a volatile diluent is employed this provides a balance of residual durability of the ultimate composition after evaporation of the volatile diluent and ease of applicability.

Preferably, the composition of the present invention including a diluent (e.g. fumed silica, non-volatile silicone fluid, diluent and pharmaceutical active agent) has a viscosity of greater than or equal to 1,000 centistokes, preferably greater than or equal to 5,000 centistokes, more preferably greater than or equal to 10,000 centistokes when measured using a glass capillary viscometer using test method ASTM D-445, IP71 at 25° C. Preferably, the composition of the present invention including a diluent has a viscosity of less than or equal to 25,000 centistokes, more preferably less than or equal to 22,000 centistokes, most preferably less than or equal to 20,000 centistokes at 25° C. when measured using a glass capillary viscometer using test method ASTM D-445, IP71.

Preferably, the composition of the present invention not including a diluent or the resultant composition formed after evaporation of a volatile diluent from the composition of the present invention including a diluent (i.e. after application) has a viscosity of greater than or equal to 27,000 centistokes, more preferably greater than or equal to 30,000 centistokes when measured at 25° C. using a glass capillary viscometer using test method ASTM D-445, IP71 at 25° C. Preferably, the composition of the present invention not including a diluent or the resultant composition formed after evaporation of a volatile diluent from the composition of the present invention including a diluent has a viscosity of less than or equal to 45,000 centistokes, more preferably less than or equal to 40,000 centistokes, most preferably less than or equal to 35,000 centistokes after evaporation of the volatile diluent when measured using a glass capillary viscometer using test method ASTM D-445, IP71 at 25° C.

Conveniently, the composition of the present invention including a volatile diluent (e.g. fumed silica, non-volatile silicone fluid, volatile diluent and pharmaceutical active agent) having an initial specific viscosity within the aforementioned limits typically attains the resultant desired final viscosity (i.e. after evaporation of the volatile diluent therefrom) by the application of body heat only. Conveniently, such a composition may be considered as "self-drying" following application to a target tissue site.

Suitably, a composition of the present invention including a volatile diluent in the form of a gel/cream having an initial viscosity of about 15,000 to 20,000 centistokes at 25° C. (ASTM D-445, IP71) produces a resultant composition having a viscosity of about 30,000 to 35,000 centistokes at 25° C. (ASTM D-445, IP71) in less than or equal to 20 minutes, more preferably less than or equal to 18 minutes, even more preferably less than or equal to 15 minutes following application of the composition to a target tissue site (i.e. when the composition is subjected to a temperature of approximately 38° C.). Suitably, a composition of the present invention including a volatile diluent in the form of a gel/cream having an initial viscosity of about 15,000 to 20,000 centistokes at 25° C. (ASTM D-445, IP71) produces a resultant composition having a viscosity of about 30,000 to 35,000 centistokes at 25° C. (ASTM D-445, IP71) in greater than 10 minutes, more preferably greater than or equal to 12 minutes following application of the composition to the target tissue site (i.e. when the composition is subjected to a temperature of approximately 38° C.).

A highly preferred composition of the present invention including a diluent comprises:
1 to 5% by weight fumed silica as defined herein;
35 to 65% by weight non-volatile silicone fluid as defined herein;
25 to 65% by weight volatile diluent as defined herein; and
1 to 5% by weight of a pharmaceutical active agent as defined herein,
wherein the component parts of the composition total 100% by weight.

Suitably, the composition of the present invention is suitable for use in medicine, particularly for the therapeutic, curative and/or prophylactic treatment of a medical condition for which the topical application of the composition is indicated. Suitable medical conditions include reducing and/or preventing scarring, ameliorating existing scars, reducing and/or preventing infection of a target tissue, such as a cut, wound or skin lesion, by a pathogen, such as bacteria, viruses and fungi. Furthermore, the composition of the present invention may be suitable for use in the therapeutic, curative and/or prophylactic treatment of eczema, psoriasis and dermatitis. Preferably, the pharmaceutical active agent possesses antibacterial, antiviral and/or antifungal activity, most preferably the pharmaceutical agent possess antibacterial activity, most preferably the pharmaceutical agent possess antibacterial activity.

According to a further aspect, the present invention provides a method for delivering a pharmaceutical active agent as defined hereinbefore to a target tissue by administering a composition of the present invention as defined hereinbefore to the target tissue. Suitably, the target tissue comprises a wound, such as a skin lesion, cut or a scar. Preferably, the composition is administered topically to the target tissue.

According to yet a further aspect, the present invention provides a method for reducing and/or preventing scarring, particularly hypertrophic or keloid scars, comprising administering a composition of the present invention as defined hereinbefore to a wound, cut, skin lesion or a scar. Conveniently, the composition of the present invention may be administered topically to the target tissue site. Suitably, the present invention provides a wound dressing comprising a composition of the present invention as defined hereinbefore. Suitably, the wound dressing may be in a form as described herein e.g. gel, stiff cream, film etc.

Conveniently, the composition of the present invention may ameliorate or reduce existing scars when applied thereto.

According to a further aspect, the present invention provides a method of manufacturing a composition of the present invention as defined herein, comprising contacting a pharmaceutical active agent as defined herein with a non-volatile silicone fluid and fumed silica as defined herein. Preferably, the pharmaceutical active agent is mixed with a blend of the non-volatile silicone fluid and fumed silica. Preferably, a diluent, particularly a volatile diluent, as defined hereinbefore is also added to the composition of the present invention.

Preferably, the compositions of the present invention are prepared by methods well known to those skilled in the art for example by using stirrers, blenders, mills and the like and other methods suitable for blending silicone oils and fumed silica. In addition, pressure vessels and condensing systems may be used to retain the volatile diluent if one is included in the composition of the present invention. Suitably, the non-volatile silicone fluid and fumed silica blend is initially prepared and then admixed with the diluent, if one is included, and the pharmaceutical active agent. Alternatively, the blend of the non-volatile silicone fluid and fumed silica and a diluent may be formed in one stage and the pharmaceutical active agent added thereto. It will be appreciated by those skilled in the art that the pharmaceutical active agent may be added at any stage of the preparation of the composition of the present invention.

Typically, when the pharmaceutical active agent represents an antibiotic zeolite a masterbatch comprising the pharmaceutical active agent, the mixture of a blend of non-volatile silicone fluid and fumed silica, and optionally the diluent as described hereinbefore, is initially prepared. Suitably, the masterbatch includes the pharmaceutical active agent at 20% by weight of the masterbatch. The masterbatch may then be diluted with the mixture of the blend of non-volatile silicone fluid and fumed silica and/or the diluent to form a composition of the present invention having the desired concentration of the pharmaceutical active agent as described hereinbefore (typically 1 to 5 wt % of the composition for an antibiotic zeolite). Advantageously, such a processing technique may ensure correct dispersion of the antibiotic zeolite in the blend of non-volatile silicone fluid and fumed silica, and optionally the diluent, whilst minimizing the agglomerization of the antibiotic zeolite, thereby resulting in an increased antibiotic activity of the composition of the present invention.

Alternatively, or additionally, a dispersant such as magnesium stearate, may be added to the masterbatch to promote dispersion of the antibiotic zeolite within the composition of the present invention. Typically, an anhydrous dispersant is mixed with the anhydrous antibiotic zeolite before compounding. Preferably, 10% by weight of the dispersant is included. The antibiotic zeolite/dispersant mixture may then be used to form a masterbatch as described hereinbefore. Preferably, particularly in the case of an antibiotic zeolite, the compositions of the present invention are prepared under anhydrous conditions as the inclusion of water in the compositions of the present invention may promote discoloration and agglomerization of the pharmaceutical active agent, thereby resulting in decreased efficiency of the composition.

According to a further aspect, the present invention provides a method for treating a wound comprising applying composition of the present invention to a wound.

According to a further aspect, the present invention provides a topical pharmaceutical delivery system comprising a composition of the present invention.

According to a further aspect, the present invention provides a wound dressing comprising a composition of the present invention. Conveniently, the wound dressing may deliver a pharmaceutical active agent to the target tissue and/or prevent, reduce or ameliorate scarring at the target tissue site.

It will be appreciated by those skilled in the art, that the compositions of the present invention may be administered by non-medical professional staff. Suitably, the compositions of the present invention are applied to the target tissue by means well known to those skilled in the art, such as application with a spatula, a roll-on or spray type applicator The invention will now be described by way of the following non-limiting examples.

The following raw materials were used:
Agion™ an antibiotic zeolite, in which the ion-exchangeable ions of the zeolite have been partially or fully exchanged with silver ions, supplied by Agion Technologies of 60 Audubon Road, Wakefield, Mass. 01880, USA;
Dow Corning 200 having a viscosity at 25° C. of about 30,000 centistokes (non-volatile silicone fluid);
Dow Corning 245 comprising polydimethylcyclosiloxane having a viscosity of 4 mm$^2$s$^{-1}$ at 25° C. (volatile diluent); and
Aerosil™ fumed silica.

EXAMPLE 1

Preparation of a Composition of the Present Invention

A masterbatch comprising 20 weight percent Agion™ and the balance of the masterbatch (80 wt %) comprising a mixture of Aerosil 200, Dow Corning 200 and Dow Corning 245 (3% by weight Aerosil 200: 50% by weight Dow Corning 200: 47% by weight Dow Corning 245) was prepared by adding the Agion™ powder to a blend of the non-volatile silicone fluid, fumed silica and volatile silicone diluent. The masterbatch was stirred with a JH Day Pony Mixer at ambient temperature, under anhydrous conditions, for up to 2 hours to effect dispersion of the Agion™ powder. The masterbatch was then diluted with the desired amount of the mixture of Aerosil 200, Dow Corning 200 and Dow Corning 245 (3% by weight: 50% by weight: 47% by weight) to form the following compositions of the present invention in the form of a gel having a viscosity of 19,000 to 21,000 centistokes at 25° C. when measured by a glass capillary viscometer by test method ASTM D-445, IP71.

|  | Agion ™ % by wt of the composition | Aerosil:Dow Corning 200:Dow Corning 245 (3:50:47) % by weight of the composition |
| --- | --- | --- |
| Example 1a | 1 | 99 |
| Example 1b | 2 | 98 |
| Example 1c | 5 | 95 |

EXAMPLE 2

Antibacterial Activity

Antibacterial activity against staphylococcus aureus was determined by incubating each of the compositions of Example 1a, Example 1b and Example 1c with the bacterial strain, *staphylococcus aureus* on a 2×2 inch agar plate, for 24 hours in the presence of oxygen. A composition comprising a mixture of 3% by weight Aerosil 200, 50% by weight Dow Corning 200 and 47% by weight Dow Corning 245 (i.e. without Agion™) was used as the control.

The results as shown in Table 1 demonstrate the enhanced antibacterial activity of the compositions of the present invention. The control sample and the assay alone (i.e. the assay not including a control sample) exhibited an increase in bacterial activity.

TABLE 1

| Sample Identification | Organism count (CFU/ml) | | Percent Reduction (%) |
|---|---|---|---|
| | Zero Contact Time | 24 Hours Contact Time | |
| ASSAY | $3.60 \times 10^4$ | $4.50 \times 10^4$ | NO REDUCTION |
| CONTROL | $3.60 \times 10^4$ | $1.01 \times 10^5$ | NO REDUCTION |
| COMPOSITION OF THE INVENTION WITH 1% AGION | $3.60 \times 10^4$ | <10* | 99.99% |
| COMPOSITION OF THE INVENTION WITH 2% AGION | $3.60 \times 10^4$ | <10* | 99.99% |
| COMPOSITION OF THE INVENTION WITH 5% AGION | $3.60 \times 10^4$ | <10* | 99.99% |

NOTE:
*<10 = Limit of detection of assay

EXAMPLE 3

In-Vivo Wand Healing/Antibacterial Activity

Three human volunteers having wounds which had started to develop into keloid scars were selected.

The composition of Example 1a (2 g) was spread over the scar of the first volunteer and the composition immobilised until sufficient volatile diluent had evaporated therefrom (approx. 15 minutes) so that the resulting composition adhered to the tissue site.

A control composition (2 g) comprising a mixture of 3% by weight Aerosil 200, 50% by weight Dow Corning and 47% by weight Dow Corning 245 was spread over the scar of the 20 second volunteer and the composition immobilised until sufficient volatile diluent had evaporated therefrom (approx. 15 minutes) so that the resulting composition adhered to the tissue site.

Agion™ powder alone (40 mg) was placed over the scar of the third volunteer and the powder immobilised on the tissue site with a transparent adhesive plaster.

Each of the patients were monitored over a 1 month period and the reduction in redness (representing a decrease in infection) and flattening of the scar (representing scar amelioration and/or prevention and/or reduction) was recorded. The results are presented in Table 2 below.

TABLE 2

| Sample | Reduction in Redness | Flattening of Scars |
|---|---|---|
| Example 1a | Immediate reduction in redness after 2 days, further decrease in redness occurred. | Steady reduction in level of scar. After one month scar showing visible signs of disappearing. |
| Control | Minor decrease in redness after 1 month. | Reduction in level of scar after 1 month but not as significant as Example 1a as scar present after 1 month and no signs of scar disappearing. |
| Agion ™ alone | Reduction in redness observed after 4 days. | A scar developed. |

The results demonstrate that the composition of the present invention not only reduces the redness of the scar (indicative of antibacterial activity) but also prevents and/or ameliorates scarring. Moreover, there appears to be a synergistic effect of antibacterial and/or scar reducing effects employing a combination of the antibiotic zeolite and the non-volatile silicone fluid/fumed silica mixture compared with employing the component parts of the composition of the present invention.

EXAMPLE 4

The following compositions as listed in Table 3 were prepared in accordance with Example 1 above except the Agion™ antibiotic zeolite was replaced with the appropriate pharmaceutical active agent.

TABLE 3

| | Pharmaceutical Active Agent (% by weight of the composition) | Aerosil:Dow Corning 200:Dow Corning 245 (3:50:47) (% by weight of the composition) |
|---|---|---|
| Example 4a | Chlorhexidine acetate (2% by wt) | 98% by wt |
| Example 4b | Benzamycin (3% by wt) | 97% by wt |
| Example 4c | Erythromycin (3% by wt) | 97% by wt |

EXAMPLE 5

The following composition comprising 2% by weight Agion™ and the balance comprising a mixture of 3% by weight Aerosil and 97% by weight Dow Corning 200 was prepared in accordance with Example 1 above. The resultant composition was in the form of a viscous gel having a viscosity of approximately 28,000 to 30,000 centistokes at 25° C. when measured by a glass capillary viscometer by test method ASTM D-455, IP71.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. A wound dressing consisting of at least one non-volatile silicone fluid in admixture with fumed silica, one or more antibacterial active agent, and at least one volatile diluent.

2. The wound dressing of claim 1, wherein said at least one non-volatile silicone fluid consists of a silicone polymer.

3. The wound dressing of claim 1, wherein said at least one non-volatile silicone fluid is present in an amount of greater than or equal to 20% by weight of the wound dressing.

4. The wound dressing of claim 1, wherein the blend of said at least one non-volatile silicone fluid and fumed silica consists of greater than or equal to 2% by weight fumed silica.

5. The wound dressing of claim 1, wherein the blend of said at least one non-volatile silicone fluid and fumed silica consists of less than or equal to 12% by weight fumed silica.

6. The wound dressing of claim 1, wherein said one or more antibacterial active agent is present in an amount of greater than or equal to 0.1% by weight of the wound dressing.

7. The wound dressing of claim 1, wherein said one or more antibacterial active agent is present in an amount of less than or equal to 50% by weight of the wound dressing.

8. The wound dressing of claim 1, wherein at least one of said one or more antibacterial active agent is in the form of a solid.

9. The wound dressing of claim 1, wherein at least one of said one or more antibacterial active agent is an antibiotic zeolite.

10. The wound dressing of claim 9, wherein the antibiotic zeolite consists of ion-exchangeable ions which have been totally or partially ion-exchanged with an antibiotic metal ion selected from the group consisting of silver ions, copper ions, zinc ions and a mixture thereof.

11. The wound dressing of claim 10, wherein the antibiotic metal ions in the zeolite are present in an amount of greater than or equal to 0.1% by weight based on the weight of the zeolite.

12. The wound dressing of claim 10, wherein the antibiotic metal ions in the zeolite are present in an amount of less than or equal to 15% by weight based on the weight of the zeolite.

13. The wound dressing of claim 1, wherein said at least one volatile diluent consists of a volatile silicone fluid.

14. The wound dressing of claim 1, wherein said at least one diluent is present in an amount of greater than 1% by weight of the wound dressing.

15. The wound dressing of claim 1, wherein the viscosity of said one or more diluent is less than or equal to 10 $mm^2s^{-1}$ at 25° C. when measured by test method ASTM D-455.

16. The wound dressing of claim 1, wherein upon evaporation of said at least one volatile diluent from the wound dressing, the resultant wound dressing has a higher viscosity.

17. The wound dressing of claim 1, wherein said at least one non-volatile silicone fluid has a viscosity of less than or equal to 200,000 centistokes when measured at 25° C.

18. The wound dressing of claim 1, wherein the wound dressing is in the form of a spreadable cream, gel, oil, light grease or mobile spray on fluid.

19. The wound dressing of claim 1, consisting of:
1 to 5% by weight fumed silica;
35 to 65% by weight non-volatile silicone fluid;
25 to 65% by weight volatile diluent; and
1 to 5% by weight of an antibacterial active agent, wherein the component parts of the wound dressing total 100% by weight.

20. A method of manufacturing the wound dressing of claim 1 consisting of contacting an antibacterial active agent with a mixture of a non-volatile silicone fluid and fumed silica.

21. A method for the prophylactic treatment, therapeutic treatment or combination thereof of a tissue site infected by a pathogen, the method consisting of applying the wound dressing of claim 1 to the tissue site.

22. A method for the prophylactic treatment, therapeutic treatment or combination thereof of a scar consisting of applying the wound dressing of claim 1 to said scar.

23. A method for delivering a pharmaceutical active agent to a target tissue, the method consisting of administering the wound dressing of claim 1 to the target tissue.

24. The method of claim 23, wherein the wound dressing is applied topically to the target tissue.

25. A method for reducing scarring, preventing scarring or a combination thereof consisting of administering the wound dressing of claim 1 to a tissue site.

26. A method for treating a wound consisting of applying the wound dressing of claim 1 to the wound.

27. A topical pharmaceutical delivery system consisting of the wound dressing of claim 1.

28. An applicator comprising a reservoir consisting of the wound dressing of claim 1, and a dispenser in fluid communication with the reservoir for dispensing the wound dressing from the reservoir.

29. The applicator of claim 28 wherein the dispenser consists of a spray, a roller ball, or a spatula.

30. The wound dressing of claim 2, wherein the silicone polymer consists of a linear dimethicone.

31. The wound dressing of claim 2, wherein the non-volatile silicone fluid is present in an amount of greater than or equal to 20% by weight of the wound dressing.

32. The wound dressing of claim 8, wherein the solid consists of a powder.

33. The method of claim 21, wherein the pathogen is bacteria or viruses.

34. The method for the prophylactic treatment, therapeutic treatment or combination thereof of a scar as claimed in claim 22, wherein the wound dressing reduces scars, prevents scars or a combination thereof within a time of one month or less.

35. A method for reducing, preventing or ameliorating scarring of damaged tissue consisting of applying the wound dressing as defined in claim 1.

36. A wound dressing consisting of at least one non-volatile silicone fluid in admixture with fumed silica, one or more antibacterial active agent, and at least one volatile diluent, said wound dressing being capable of ameliorating, preventing, or reversing the formation of scarring at a tissue site when said wound dressing is made to contact the site.

37. A method of manufacturing the wound dressing of claim 1 consisting of contacting an antibacterial active agent with a mixture of a non-volatile silicone fluid and fumed silica, and adding a diluent to the mixture thereof.

* * * * *